United States Patent [19]

Roth et al.

[11] Patent Number: 4,817,601

[45] Date of Patent: Apr. 4, 1989

[54] CATHETER SYSTEM FOR CONTROLLED REMOVAL BY RADIANT ENERGY OF BIOLOGICAL OBSTRUCTIONS

[75] Inventors: Laurence A. Roth, Londonderry, N.H.; Stephen J. Herman, Andover, Mass.; Carl R. Turnquist, Concord, Mass.; Edward L. Sinofsky, Reading, Mass.; Jacob Y. Wong, Santa Barbara, Calif.

[73] Assignee: C. R. Bard, Inc., Murray Hill, N.J.

[21] Appl. No.: 47,430

[22] Filed: May 6, 1987

Related U.S. Application Data

[63] Continuation of Ser. No. 708,826, Mar. 6, 1985, abandoned.

[51] Int. Cl.$^4$ ............................................. A61B 17/36
[52] U.S. Cl. ................................................ 128/303.1
[58] Field of Search ........................................ 128/4-8, 128/303.1, 395-398; 350/96.26; 604/158

[56] References Cited

U.S. PATENT DOCUMENTS

| | | | |
|---|---|---|---|
| 3,821,510 | 6/1974 | Muncheryen | 128/303.1 |
| 4,036,218 | 7/1977 | Yamashita et al. | 128/4 |
| 4,207,874 | 1/1980 | Choy | 128/303.1 |
| 4,211,229 | 7/1980 | Wurster | 128/303.1 |
| 4,266,534 | 5/1981 | Ogawa | 128/6 |
| 4,273,109 | 6/1981 | Enderby | 128/6 |
| 4,421,382 | 12/1983 | Doi et al. | 128/303.1 |
| 4,431,426 | 2/1984 | Groshong et al. | 604/280 |
| 4,448,188 | 5/1984 | Loeb | 128/303.1 |
| 4,517,974 | 5/1985 | Tanner | 128/303.1 |
| 4,558,691 | 12/1985 | Okada | 128/6 |
| 4,587,972 | 5/1986 | Moranth | 128/303.1 |
| 4,592,353 | 6/1986 | Daikurono | 128/303.1 |

FOREIGN PATENT DOCUMENTS

| | | |
|---|---|---|
| 0153847 | 4/1985 | European Pat. Off. . |
| 0144764 | 6/1985 | European Pat. Off. . |
| 14079 | 10/1955 | Fed. Rep. of Germany ......... 128/4 |
| 686725 | 9/1979 | U.S.S.R. ................................... 128/4 |
| 683721 | 9/1979 | U.S.S.R. ................................... 128/4 |
| 1417906 | 12/1975 | United Kingdom . |
| 2030313 | 6/1979 | United Kingdom .................... 128/4 |
| 8500510 | 2/1985 | World Int. Prop. O. . |
| 8505262 | 12/1985 | World Int. Prop. O. . |

OTHER PUBLICATIONS

"Ultraviolet-Laser Ablation of Skin" Linsker et al. Archives of Dermatology.

Primary Examiner—Max Hindenburg
Attorney, Agent, or Firm—Wolf, Greenfield & Sacks

[57] ABSTRACT

A catheter for delivering radiant energy, such as a laser beam, is used in a technique to controllably apply the radiant energy in a patient's body, such as in a blood vessel. The radiant energy is applied in a manner which erodes biological material and may be used to drill through vascular obstructions. The catheter emits the radiant energy from its distal end in a pattern which defines a relatively small working region in which the energy density level is sufficiently high to remove the biological material. The energy distribution is substantially uniform across the beam. Distally beyond the working region, the energy density of the beam decays sharply so that biological material beyond the working region is not removed.

50 Claims, 6 Drawing Sheets

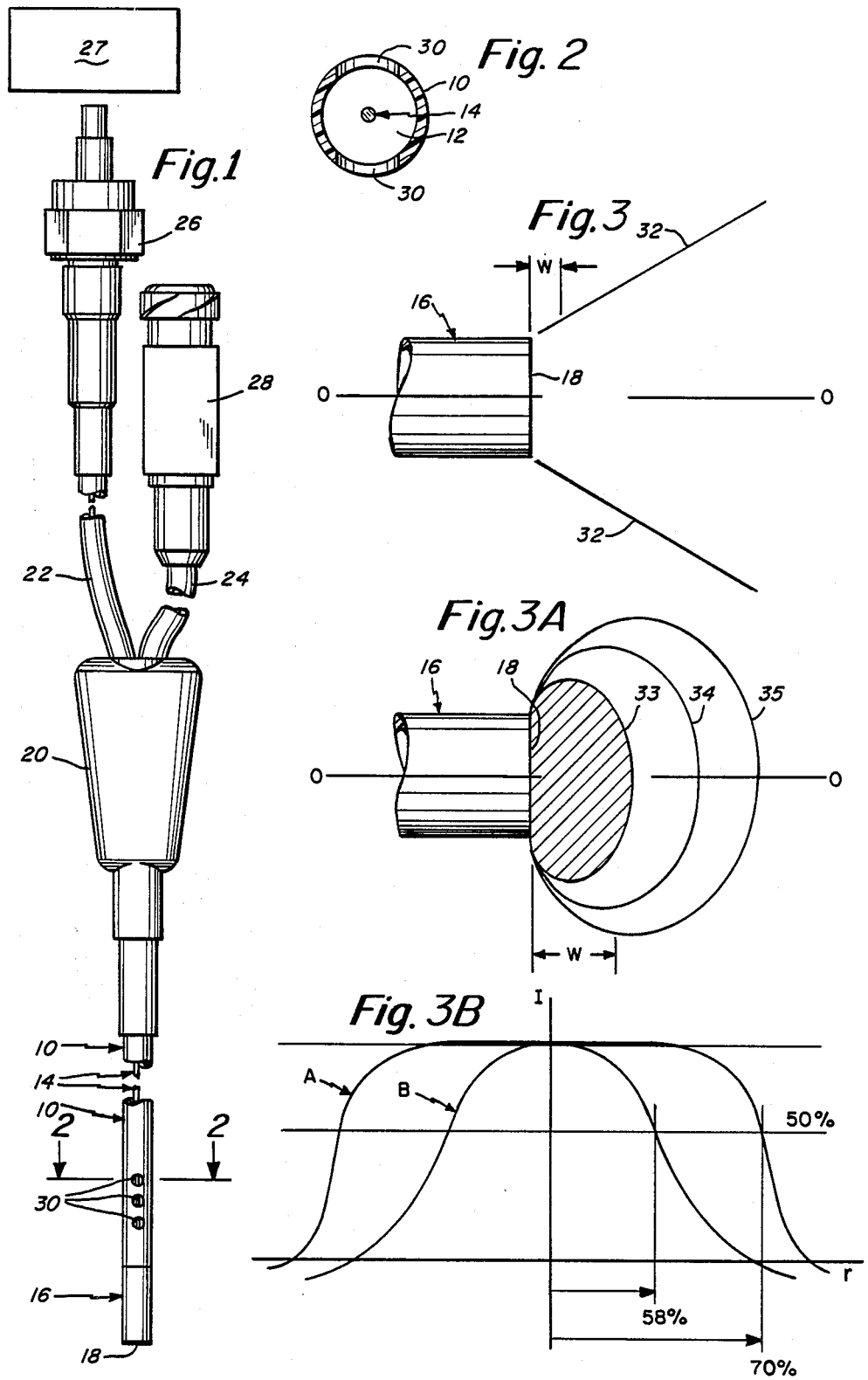

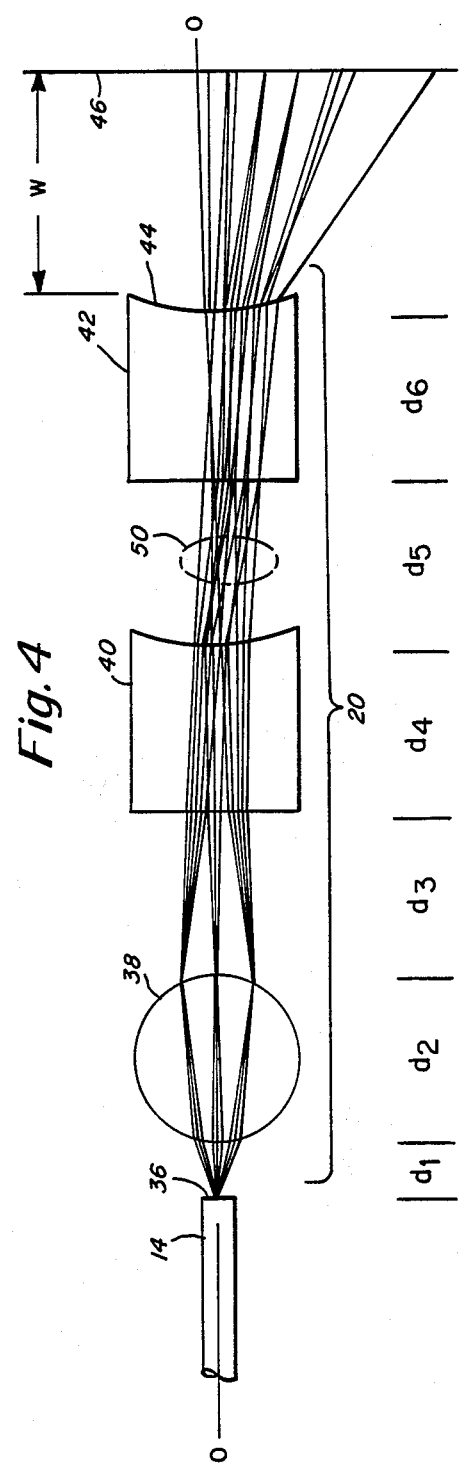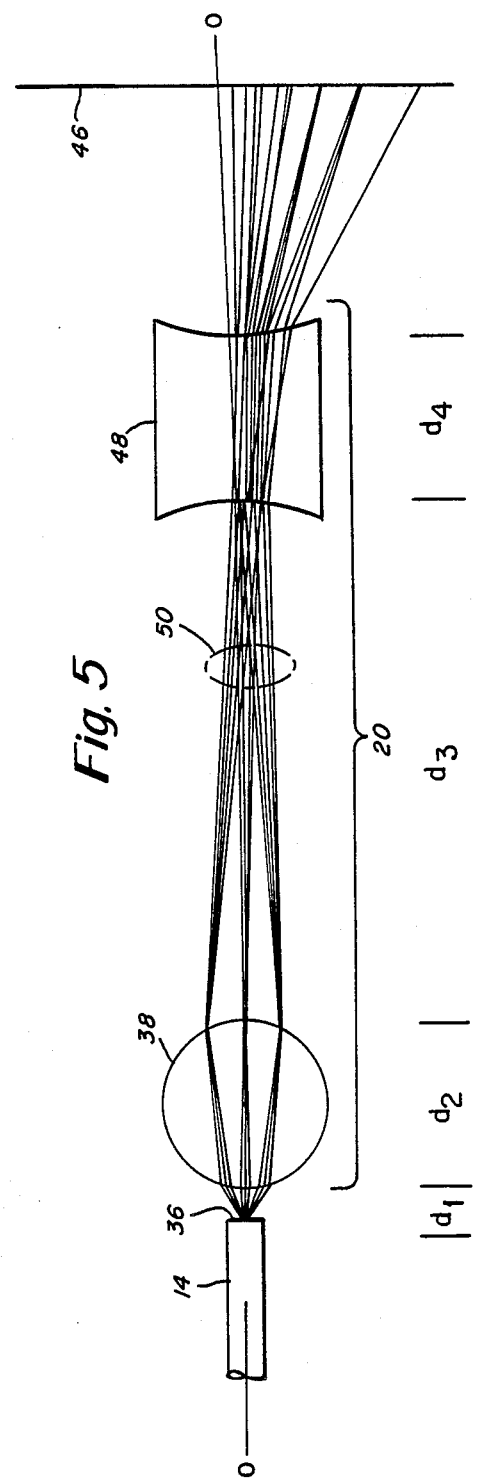
Fig. 4
Fig. 5

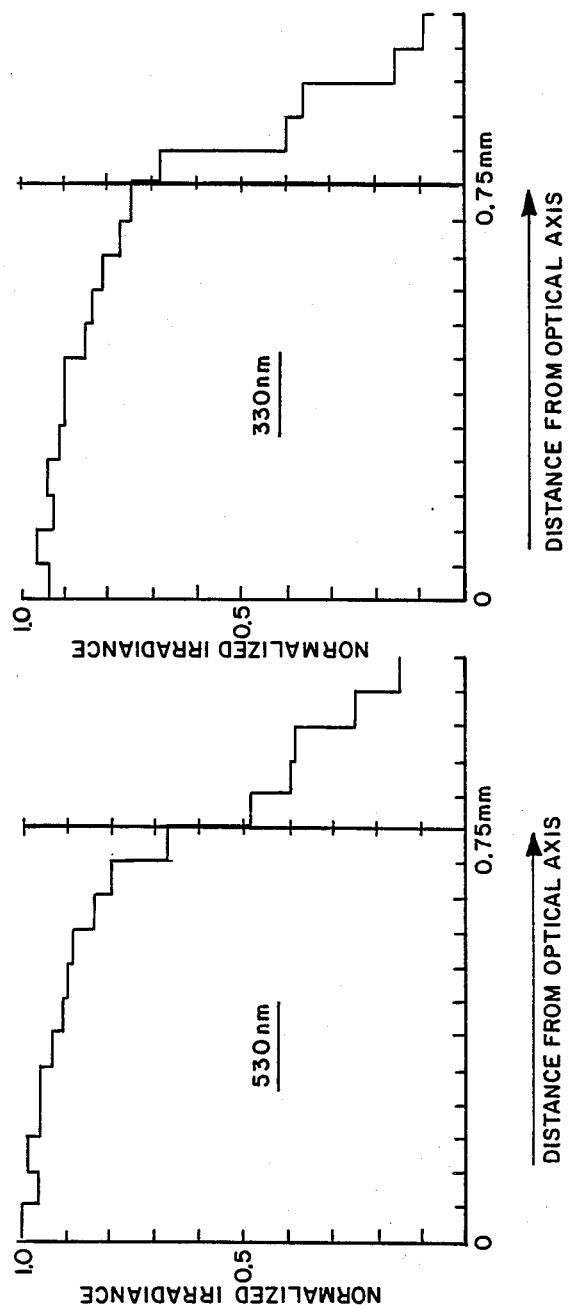

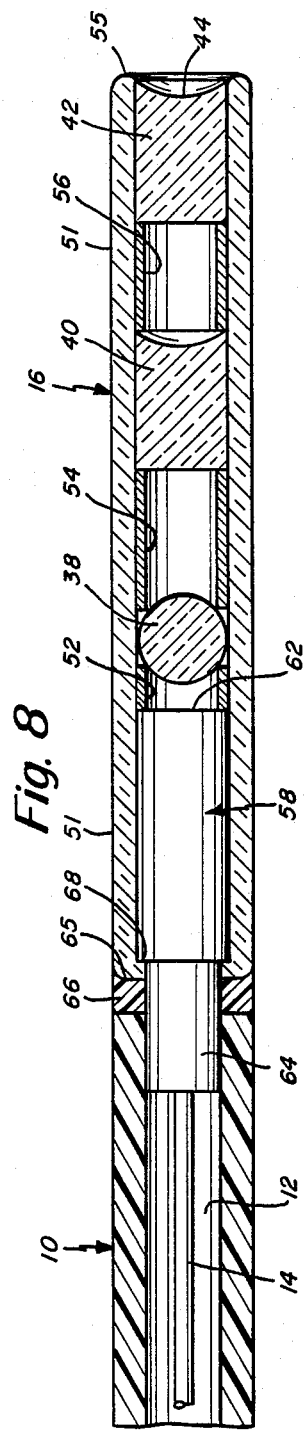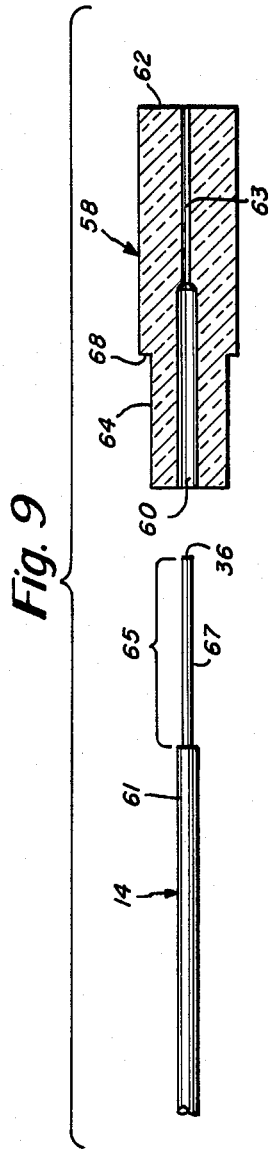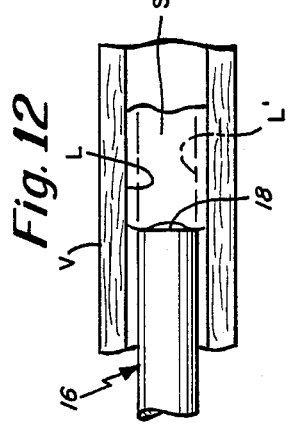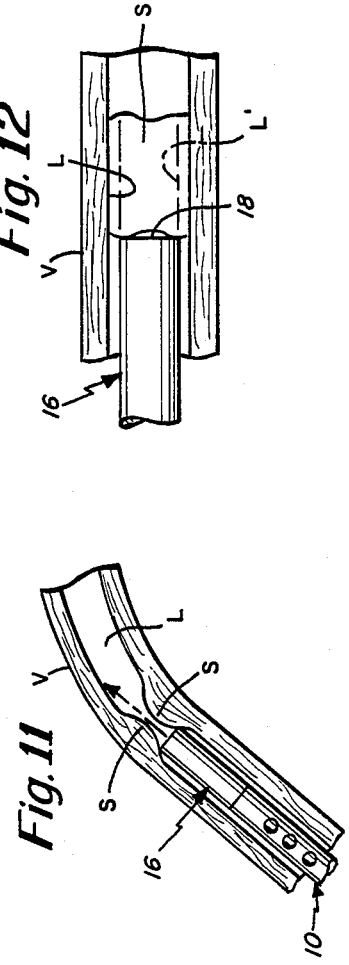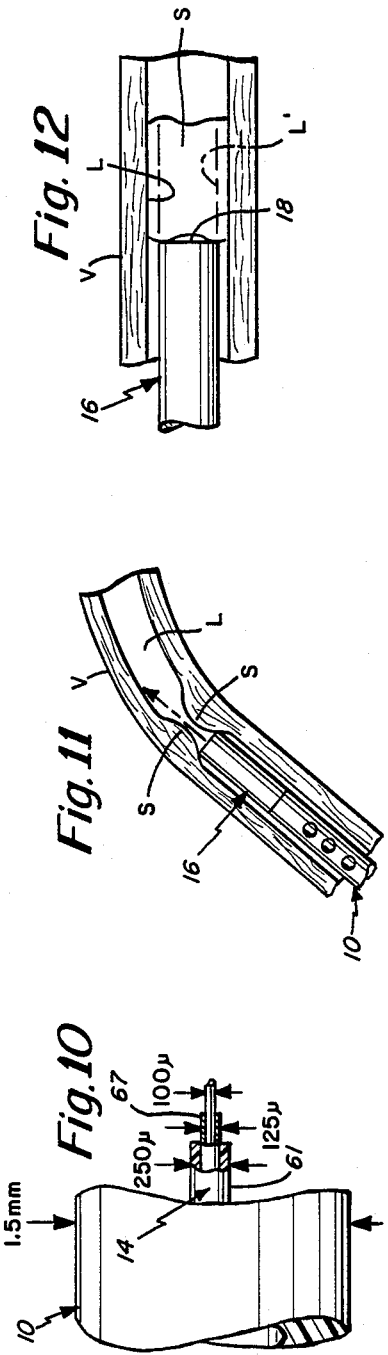

CATHETER SYSTEM FOR CONTROLLED REMOVAL BY RADIANT ENERGY OF BIOLOGICAL OBSTRUCTIONS

This application is a continuation of application Ser. No. 708,826, filed 3/6/85, now abandoned.

FIELD OF THE INVENTION

This invention relates to catheters and techniques for delivering and applying radiant energy, such as in the form of a laser beam, to the human body for controlled and selective removal of tissue, plaque and other biological material.

BACKGROUND OF THE INVENTION

This invention relates to the use and application of radiant energy within the human body for the controlled removal or etching away, for example, by ablation, of tissue or other biological material, in particular the removal of a vascular obstruction. The treatment of vascular obstructions including peripheral as well as coronary vascular obstructions, has been the subject of much investigation in recent years. Vascular surgery in which a diseased vessel is removed and replaced with a graft, or in which the blocked region of the vessel is bypassed with a graft, has become relatively common. Nevertheless, it is desirable that procedures and techniques be improved to reduce the level of trauma to a patient so as to simplify the procedure and treatment for the patient but without sacrificing effectiveness. While procedures for surgical removal and by-passing of vascular obstructions have become well developed, it clearly is desirable to provide alternatives to such nonconventional surgical procedures.

Among the alternatives which have been developed is the angioplasty procedure in which devices such as the balloon dilatation catheter of the type illustrated in Gruntzig U.S. Pat. No. 4,195,637, are used to open a passage through a vascular obstruction. In the balloon dilatation technique a catheter having a special balloon at its distal end is advanced through the patient's blood vessels until the balloon is placed within the obstruction. The balloon then is expanded under substantial pressure to forcibly enlarge the lumen within the blood vessel. When the procedure is successful the lumen of the blood vessel remains open after the balloon has been deflated and removed. The material which caused the obstruction, typically arterial plaque, is compressed radially outwardly. Those patients who can be treated successfully with the dilatation technique are spared the trauma, time and expense of traditional vascular surgery. However, the angioplasty technique cannot be used to treat all vascular obstructions and, indeed, the majority of obstructions cannot be treated in that manner.

When an obstructed vessel is treated surgically by replacement or bypass of the vessel, the diseased portion of the vessel either is removed in its entirety or is permitted to remain, in its obstructed condition, in the patient but with a bypass vessel grafted across the blocked regions. In the angioplasty technique the plaque which formed the obstruction remains in the artery although in a compressed condition. In some instances the plaque and vessel wall may rearrange themselves after some time to begin to obstruct the vessel again.

Although the general desirability of recanalizing an obstructed blood vessel by removal of the vascular obstructions from the vessel has long been recognized, no effective system or treatment technique has yet been discovered or developed for that purpose. The possibility of using laser energy for that purpose also has been recognized for some time. While recent availability of laser sources of controllable radiant energy have been found useful for some surgical operations, such as in certain kinds of eye surgery, no suitable device and technique have been developed by which a beam of radiant energy such as laser energy can be applied to a vascular obstruction to selectively and controllably remove that obstruction without causing trauma to the vessel, so as to leave the natural vessel in a healthy, unblocked, recanalized and functioning condition.

Proposals and efforts to apply laser energy to remove a vascular obstruction have encountered numerous difficulties. Prior efforts to deliver a beam of laser energy typically have involved the use of various configurations of catheters having arrangements of fiber optical conductors to conduct the radiant energy into the patient's vessel in an effort to direct the beam to the obstruction so as to destroy the obstruction. No devices or techniques have been developed by which it was possible to control effectively the beam. If the beam is not aligned properly in the blood vessel it can impinge against the lining of the blood vessel thereby damaging the vessel wall and possibly puncture the wall. Even if the beam is aligned properly in the blood vessel, the lining of the vessel can be damaged or the vessel can be punctured if there is a bend in the vessel just distal of the location of the obstruction.

Also among the significant difficulties encountered in trying to use laser energy to clear vascular obstructions is the tendency of the laser beam to cause biological material to char in the region surrounding the target. Such charring results, at least in part, from poor control over the manner and amount of energy applied. In the context of a delicate blood vessel, charring can present very serious problems, possibly doing severe damage to the surrounding tissue. Additionally, any biological material which becomes charred and adheres to the distal tip of the optical fiber conductor prevents emission of the beam from the distal tip of the conductor. In that case, the material at the end of the conductor becomes highly heated which, in turn, causes overheating and destruction of the optical fiber.

Other difficulties relate to the manner of positioning and locating the distal end of the catheter so that it is positioned properly with respect to the obstruction. Prior proposals which have included the use of supplemental optical fibers to transmit illuminating light into the blood vessel in conjunction with other groups of fibers to permit visual observation of the interior of the blood vessel are not practical because they are too large and too stiff for use in coronary arteries. Another difficulty is that there often may be material such as blood in the region between the emission point of the laser beam at the end of the fiber and the obstruction. Such material may obstruct the optical path. The blood may become charred at the distal emitting tip of the fiber which, as described above, can result in overheating and destruction of the optical fiber.

All of the foregoing difficulties have been complicated by the dimensional limitations imposed on any catheter which is to be inserted into a blood vessel, particularly narrow blood vessels such as coronary arteries which can have lumens of the order of 1.5 to 4.5 millimeters diameter.

The present invention relates to new catheter systems for delivering radiant energy to a selected site within a blood vessel in a manner which enables the radiant energy to be applied controllably to an obstruction and in a manner which avoids the foregoing and other difficulties.

SUMMARY OF THE INVENTION

The invention relates to new methods and means for delivering radiant energy from a source to a site within a patient's blood vessel where the energy is to be applied. More particularly, the invention concerns new methods and devices including a new catheter having a fiber optics conductor to deliver radiant energy (e.g., from a laser) to the site to be treated. The catheter has, at its distal end, a miniature optical system to controllably apply the radiant energy at the site. The optical system and catheter are arranged so that the radiant energy is distributed substantially uniformly in a beam which combines an exponentially decaying energy level with a geometrically expanding beam pattern. The optical system controls the beam to define a working region surrounding the axis of the propagation direction of the energy in which the removal of biological material takes place in a very limited layer-like region transverse to that axis.

A system for practising the invention includes an elongate, small diameter catheter having a lumen which carries an optical fiber. The proximal end of the catheter has a connector by which the optical fiber may be connected to receive the radiant energy output from a laser. The distal end of the catheter has an optical housing which incorporates a net negative optical power lens system arranged to emit a beam of radiant energy in an expanding (divergent), unfocused pattern. The energy distribution is substantially uniform Over the cross-section of the expanding beam. The beam has a short segment which extends a short distance from the distal emission aperture of the optical system and defines the working region in which the radiant energy is at a high enough level to remove the biological material. Depending on the frequency of the radiant energy and the absorption properties of the biological material, thermal disassociation or ablative photo-decomposition may be employed as the dominant etching or eroding mechanism. Distally beyond the working region the exponentially decaying beam diverges to a lower, safe energy density which will minimize damage to the biological material.

The depth of the working region as measured along the optical axis of the projected beam varies somewhat depending on the index of refraction of a light-propagating medium into which the beam is projected; up to about 1 to 1.5 mm is preferred. A medium having a greater index of refraction will tend to decrease the divergence of the beam thereby increasing the depth of the working region in the direction of the optical axis. The optical system is arranged so that the maximum depth of the working region is relatively short, of the order of 1.5 millimeters maximum depth, so that a distally propagated segment of the beam will not have sufficient energy level to puncture the vessel wall. The maximum diameter of the working region is not smaller than and may be slightly greater than the catheter diameter to enable the catheter to advance through the hole which the beam will form through the obstructing material.

The optical system at the distal end of the catheter includes a housing which contains one or more lenses spaced from each other by radiopaque spacers. The use of radiopaque spacers enables the catheter to be positioned in the blood vessel accurately by fluoroscopy. A special internal holder is provided to receive and securely position the distal end of the optical fiber rigidly with respect to the optical components in the housing. The manner in which the optical fiber is mounted isolates completely the distal end of the optical fiber from the blood vessel. That completely avoids the possibility of biological material contacting the distal tip of the optical fiber which might result in formation of a char on the tip with resulting destruction of the optical fiber.

The spacers and the housing cooperate to provide optical precision in a miniature environment. The catheter is arranged so that the distal tip of the optical housing may be advanced into direct contact with the vascular obstruction. This assures that there will be little or no optically obstructing material between the distal tip of the catheter and the vascular obstruction and also assures that the distal tip of the catheter will be positioned properly with respect to the obstruction.

The catheter may be provided with a lumen by which liquid may be flushed into and aspirated from the operative site in the blood vessel to draw away debris which may be developed during the removal procedure.

It is among the objects of the invention to provide a catheter adapted to deliver radiant energy into a blood vessel to enable forming a hole in vascular obstructions, and the effective removal of such obstructions.

Another object of the invention is to provide a catheter of the type described which is arranged to emit the radiant energy from an emission aperture at the distal end of the catheter in a pattern which minimizes the risk of undue injury to or puncture of the wall of the blood vessel.

Another object of the invention is to provide a device of the type described in which the distal end of the catheter may be placed and oriented accurately with respect to the targeted obstruction by fluoroscopic means, and without requiring the use of endoscopic visualization systems.

A further object of the invention is to provide a device of the type described in which the pattern Of the beam emitted from the distal tip Of the catheter is arranged to form an aperture in an Obstruction not substantially greater than the catheter diameter but large enough to permit the catheter to be advanced through the obstruction.

Another object of the invention is to provide a device of the type described in which the distal tip of the optical fiber is completely isolated from biological material.

A further object of the invention is to provide a catheter of the type described having a miniature optical system at the distal end of the catheter.

Another object of the invention is to achieve the foregoing and other objects within a catheter of very small diameter.

BRIEF DESCRIPTION OF THE DRAWINGS

The foregoing and other objects and advantages of the invention will be appreciated more fully from the following further description thereof, with reference to the accompanying drawings wherein:

FIG. 1 illustrates generally a catheter according to the invention;

FIG. 2 is a section taken on line 2—2 in FIG. 1;

FIG. 3 is a diagrammatic illustration of the distal tip of the catheter showing the divergent beam pattern emitted from the optical housing; FIG. 3A schematically illustrates the thermal profile of a heat pattern created in an absorbing medium in response to the combined exponentially decaying energy and geometrically expanding beam pattern which is provided by the invention;

FIG. 3B is a graphic representation comparing energy distribution according to the invention with a Gaussian energy distribution;

FIG. 4 is an optical-schematic view, greatly enlarged, of an optical system of the invention and its relation to the distal end of the optical fiber;

FIG. 5 is an optical-schematic view similar to that of FIG. 3 illustrating another embodiment of the optical system;

FIGS. 6A and 6B are energy distribution plots illustrating substantially uniform energy distribution in the working portion of the energy beam for the system illustrated in FIG. 4;

FIG. 8 is a greatly enlarged sectional side view of the distal end of the catheter including an optical system assembly according to the invention;

FIG. 9 illustrates in further detail, the fiber holder and distal tip of the fiber shown in the assembly of FIG. 8;

FIG. 10 illustrates dimensional details of the fiber optics conductor;

FIG. 11 is a diagrammatic illustration of the distal end of the catheter in a partially stenosed blood vessel;

FIG. 12 is another diagrammatic illustration of the distal end of the catheter in abutment with the stenosis in a fully obstructed blood vessel.

DETAILED DESCRIPTION OF THE ILLUSTRATIVE EMBODIMENTS

Figure 7B:
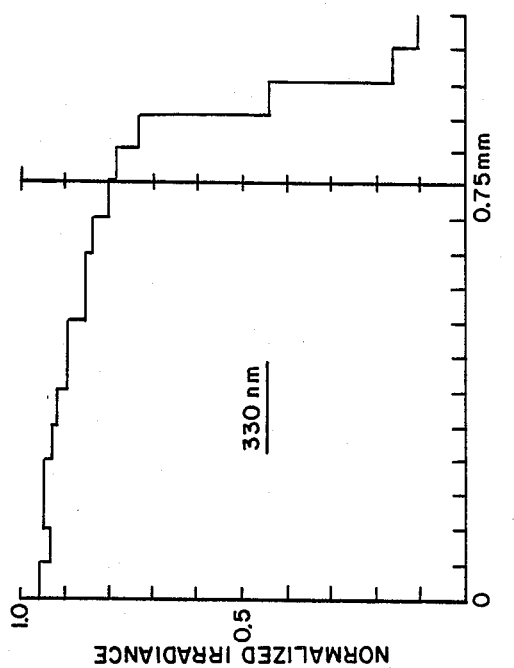
FIGS. 7A and 7B are energy distribution plots illustrating substantially uniform energy distribution at the working portion of the energy beam for the optical system illustrated in FIG. 5.

As is shown generally in FIGS. 1 and 2, the catheter is formed from an elongate flexible body 10 and, for example, may be extruded from an appropriate plastic material such as Teflon (trade name for polytetrafluoroethylene). The body 10 has a lumen 12 for enclosing a fiber optic light conductor 14. The distal end of the catheter is provided with an optical housing indicated generally at 16 which contains a net-negative optical lens system. The optical system in the housing receives radiant energy from the distal tip of the fiber optic light conductor 14. The radiant energy is emitted from the optical system in a controlled predetermined pattern from an emission aperture 18.

The proximal end of the catheter includes a molded fitting 20 which is secured to the catheter body 10. Projecting from the proximal end of the fitting 20 are a pair of flexible tubes 22, 24. The tube 22 is adapted to receive the fiber optic light conductor 14, which extends through the fitting 20. The proximal end of the tube 22 is provided with a connector 26 which is connected to the proximal end of the fiber optic light conductor 14. Connector 26 is adapted to be mounted with respect to the source of radiant energy, such as a laser (illustrated diagrammatically at 27) so that the proximal end of the light conductor 14 may receive the radiant energy and conduct it along its length to the optical system 16. The other tube 24 communicates through the fitting 20 with the lumen 12 of the catheter body 10 and preferably is provided with a conventional luer connector 28.

The catheter body is provided with a plurality of fluid flow apertures 30 near the distal end. The pathway defined between the luer connector 28, tube 24, main catheter body 10 and apertures 30 provide for communication with the distal region of the patient's blood vessel where the distal end of the catheter is located. It provides a passageway for fluids or gases to flow both to and from the distal region of the patient's blood vessel and also provides a means for making pressure measurements.

In accordance with the invention the optical system forms the beam of radiation so that the beam will be unfocused and will expand geometrically for example, at an angle of about 20° to the optical beam axis 0—0, in saline solution as it leaves the emission aperture 18. FIG. 3 illustrates diagrammatically at 32 the peripheral rays of the beam when the beam is emitted into a saline solution, while FIG. 3A illustrates the response of the material to the energy pattern of the beam with respect to propagation distance from the emission aperture 18. From FIG. 3 it will be appreciated that, owing to the geometrical expansion of the beam along the beam axis, the energy density of the emitted beam decreases in a distal direction along the beam axis 0—0, while the cross-sectional area of the beam increases with propagation along the axis. This decrease in energy density is in addition to the exponential decay in energy level that is due directly to increasing propagation distance.

In accordance with the present invention, the relatively small diameter region adjacent the emission aperture 18, indicated at W in FIG. 3 and FIG. 3A, is considered to be the working region in which the energy density is sufficient to remove obstructing biological material. From FIG. 3 it will be appreciated that the working region W is comparatively short when the radiation beam is emitted into a low refraction medium such as clear saline solution (not shown). When the beam is emitted into such a medium, the optical system causes the beam to diverge at the aforesaid angle (e.g.: 20°) which assures that its effective working power density preferably will not extend more than a millimeter or two beyond the emission aperture 18. When the emission aperture is brought close enough to biological material (e.g., thrombus, plaque, blood) so that the latter is in the working region W, the beam will operate on (i.e.: remove by thermal, ablative, or other action) the biological material that is in the working region.

From the thermal profile shown in FIG. 3A, it will be appreciated that the invention combines an exponentially decaying energy profile with a geometrically expanding beam pattern, which assures a larger decrease in energy density along the optical axis 0—0 than would be available from a converging or a collimated beam pattern. The thermal profile in an absorbing medium is represented in FIG. 3A by isothermal lines 33, 34 and 35, respectively. The shaded region within the first isothermal line 33 is the thermal response within the working region W. Within that region the energy density, in Joules per cubic centimeter of spatial volume, preferably should exceed 3000 J/cm$^3$, so that the biological material in the working region will be removed (as by ablation, erosion, etc.). Between the first and second isothermal lines 33 and 34, the energy density falls off to a range between 3000 J/cm$^3$ and 272 J/cm$^3$, in which the temperature of the biological material will be about 100° C. Outside the third isothermal line, the temperature of biological material will be less than 50° C. A temperature of 50° C. or above will cause irreversible protein denaturization. When the temperature is below 50° C., cell trauma typically is insignificant and self reversing.

Within the working region W, the output beam has a substantially uniform energy distribution with respect to displacement from the beam axis 0—0. By way of example, the beam has more than 50% irradiance for radial distances of up to about 70% of the 1/$e^2$ beam radius, as is represented in curve A in FIG. 3B. Examples of such an irradiance profile are illustrated in FIGS. 6 and 7. By contrast if the energy distribution of the beam were non-uniform, such as Gaussian, its 50% irradiance point would be located at 58% of the 1$e^2$ radius as is represented in Curve B in FIG. 3B.

As has been mentioned above, the axial length of the working region W may vary somewhat, depending on the index of refraction of the medium in the working region (e.g.: saline solution) into which it irradiates before being brought to the biological material. An outer limit for the length W is selected to be at a predetermined value which will reduce the chance of projecting the energy beam in a manner which might risk serious damage to biological material located beyond the target, i.e.: more than about one to two millimeters away, so as to minimize the chance of damaging an artery, or other blood vessel. By way of example, for a 1.0 to 1.5 millimeter diameter catheter intended to be used in small bore arteries such as coronary arteries, a maximum length for the working region W of the order of 1.5 millimeters appears desirable.

Further in accordance with the invention, it will be understood that in an imaginary plane transverse to the optical axis 0—0 located about 1.5 mm. in front of the emission aperture 18, the energy density of the emitted beam is substantially uniformly distributed throughout an imaginary circle which is diametrically larger than the catheter 10. The energy density proximal of and within that circle is adequate to remove biological material so as to form a hole through which the catheter can be advanced. For example, pulses from an argon source, delivered at 25 watt/sec., 25% duty cycle, in a beam 1 mm. in diameter, through a saline solution, will remove about 0.25 mm depth of non-calcific plaque per pulse, across the beam diameter. When the beam perforates or otherwise passes distally beyond the obstruction and the fluid beyond the hole is transparent (e.g.: saline solution), the density of energy which propagates more than about 1.5 mm. beyond the obstruction will be too low to vaporize other more distant material, such as the wall of a blood vessel.

FIGS. 11 and 12 illustrate somewhat diagrammatically the manner in which the catheter is applied to vascular obstructions. As shown in FIG. 11 the blood vessel V has a lumen L which is partially obstructed by a stenosis S. The catheter is advanced through the patient's vascular system to bring the distal tip of the optical system 16 directly against the stenosis S. FIG. 12 illustrates an enlarged detail of the distal tip of the optical system 16 as it is brought to bear against a totally-blocking stenosis S within the lumen L of a blood vessel. In accordance with the invention, radiant energy emitted from the emission aperture 18 at the distal tip of the optical system 16 will ablate or otherwise remove the stenotic material S. As the catheter is advanced through the blood vessel V and as the radiant energy is applied, preferably in pulses of suitable peak power, discrete layers of the stenotic material will be removed so as to ultimately form a tunnel through the stenotic material S. The recanalized lumen formed by the tunnel is suggested diagrammatically in phantom at L' in FIG. 12. The recanalized tunnel L' thus formed is, as mentioned, slightly greater in diameter than the diameter of the catheter 10 to facilitate advancement of the catheter through the blood vessel.

The condition illustrated in FIG. 11 in which the stenosis does not block completely the lumen L of the blood vessel V, may permit some of the radiant energy to pass through the opening in the stenosis so as to be directed toward a distal portion of the inner surface of the blood vessel wall. While that would not be likely to occur if the region distal of the catheter tip is filled with relatively opaque, radiant energy absorbing fluid, it is contemplated that the system may be used with a saline flushing technique and some of the region of the lumen distal of the catheter tip might be filled with a more clear saline liquid, allowing transmission of the radiant energy. Thus, in some circumstances such as where a distal portion of the blood vessel V is curved, as illustrated in FIG. 11, the present invention minimizes the risk that radiant energy which might impinge on a distal portion of the blood vessel wall will not perforate that wall.

FIGS. 4 and 5 illustrate two embodiments of the optical system 16. As shown in FIG. 4 the light-output end 36 of the fiber optics conductor 14 is coupled to a spherical lens 38, a first plano-concave lens 40 and a second plano-concave lens 42, in succession. The inter-component spacings and component thicknesses along the optical axis 0—0 of the system are indicated on the figure as $d_1$ to $d_6$, respectively. Representative design parameters for the optical system of FIG. 4 are stated in Table I, following:

TABLE I

Design Parameters for Optical System FIG. 4

| Optical Fiber | Component Spacings & Thicknesses |
|---|---|
| Numerical Aperture = 0.3 | $d_1$ 0.3574 mm |
| Exit Diameter = 0.1 mm | $d_2$ = 1.00 mm |
| S.S.(Substantially Uniform | $d_3$ = 1.00 mm |
| (Distribution Characteristic | $d_4$ = 1.00 mm |
| | $d_5$ = 1.00 mm |
| | $d_6$ = 1.00 mm |
| | Total Length = 5.3574 mm |

| Lens | Type | Material | n (530 nm) | Radius of Curvature | Thickness |
|---|---|---|---|---|---|

TABLE I-continued

| | | Design Parameters for Optical System FIG. 4 | | | |
|---|---|---|---|---|---|
| 38 | Sphere | BK-7 | 1.5200 | $r_1$ = 0.5 mm | $d_2$ |
| 40 | Plano-concave | BK-7 | 1.5200 | $r_2$ = 1.156 mm | $d_4$ |
| 42 | Plano-concave | Corning 7740 | 1.477 | $r_3$ = 0.867 mm | $d_6$ |

The operative portion of the radiation from the system shown in FIG. 4 is located within the region W extending about 1.5. mm from the concave surface 44 of the exit lens 42, which for purposes of illustration is shown bounded by a transverse plane indicated by line 46. Shown also in FIG. 4 are ray tracings 50 from the lower half (below the optical axis 0—0 as seen in the figure) of the light output end 36 of fiber optics conductor 14 to the boundary plane 46, for a wavelength of 530 nm. In order to see the entire ray distribution at the boundary plane one can superimpose a mirror image of the traced rays with respect to the optical axis. The aperture stop is fixed at the back surface of the spherical lens 38, for ray-tracing purposes.

The ray-tracing method used in development of FIG. 4 was consistent with the assumption that the optical fiber 14 behaves like a uniform energy distribution source, to find out the approximate energy distribution at the boundary plane 46. The upper half of the optical fiber tip 36 (0.05 mm in extent) was first divided into 200 point sources. Five rays from each point source (1,000 total) spanning the numerical aperture of 0.3 were traced through the optical system 20 to the boundary plane 46. The distance between the optical axis 0—0 and the outermost dimension (0.75 mm from the optical axis) of the fiber optics conductor-lens system at the boundary plane was divided into twelve equal compartments to collect the traced rays. The number of rays which landed in each of these twelve compartments, indicative of beam intensity, are plotted as histograms in FIGS. 6A and 6B, for the wavelengths 530 mm and 330 nm, respectively. Assuming that each ray carries the same amount of energy, the histograms in FIGS. 6A and 6B approximate the energy distribution at the boundary plane 46 for the optical system shown in FIG. 4. It can be seen from FIG. 6 that this system creates an approximately 1.5 mm diameter spot of substantially uniform energy distribution in cross-section, e.g., at the boundary plane 46, 1.5 mm from the concave surface 44 of the exit lens 42. FIG. 6A is an energy distribution plot at the boundary plane for light of wavelength equal to 530 nm. The same plot for 330 nm radiant energy is shown in FIG. 6B.

FIG. 5 illustrates another embodiment of the optical system 16, in which the spherical lens 38 is followed by a single bi-concave lens 48. Otherwise the system of FIG. 5 is similar to the system of FIG. 4. Design parameters for the system in FIG. 5 are stated in Table II following:

TABLE II

| Design Parameters for Optical System FIG. 5 | |
|---|---|
| Optical Fiber | Lens Spacings & Thicknesses |
| Numerical Aperture = 0.3 | $d_1$ = 0.31 mm |
| Exit Diameter = 0.1 mm | $d_2$ = 1.00 mm |
| Substantially Uniform Energy | $d_3$ = 3.19 mm |
| Distribution Characteristic | $d_4$ = 1.00 mm |
| | Total Length = 5.50 mm |

| Lens | Type | Material | n (530 nm) | Radius of Curvature | Thickness |
|---|---|---|---|---|---|
| 38 | Sphere | BK-7 | 1.5200 | $r_1$ = 0.5 mm | $d_2$ |

TABLE II-continued

| | | Design Parameters for Optical System FIG. 5 | | | |
|---|---|---|---|---|---|
| 48 | Bi-Concave | Corning 7740 | 1.477 | $r_{21}$ = 1.092 mm $r_{31}$ = 1.158 mm | $d_4$ |

Figure 7A:
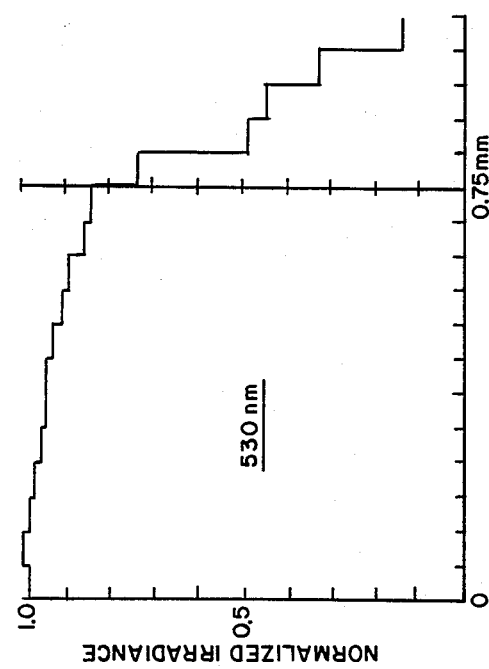

Energy distribution in the boundary plane 46, for the embodiment of FIG. 5 is shown in FIGS. 7A and 7B for wavelengths 530 nm and 330 nm, respectively. The designs of the systems shown FIGS. 4 and 5 will work particularly well for wavelenqths of light in the range from 330 nm to 530 nm, but are not limited to that range.

As can be seen from the dimensions in Tables I and II, the optical system 16 is miniature. The system of FIG. 4 has a total length of 5.36 mm; that of FIG. 5 is 5.50 mm long. Each system including the housing for the lenses is only 1.5 mm in diameter.

FIGS. 8 to 10 inclusive, show an optical assembly 16 which facilitates assembly of the lens components 38, 40 and 42 with the required spatial and positioning precision. A glass tube 51 snugly encloses the optical elements, which are spaced apart in the tube with tubular spacers 52, 54 and 56. A holder 58 for the fiber optics conductor 14 is fitted into one end of the tube 51, followed by the first spacer 52 which holds the spherical lens 28 the required distance from the aperture surface 36 of the fiber optics light conductor 14. The next spacer 54 establishes the spacing between the spherical lens and the intermediate plano-convex lens 40. The last spacer 56 establishes the spacing between the intermediate lens and the exit lens 42.

To assure that the distal end of the fiber optics conductor 14 is spaced and oriented in a precise position with respect to the optical system 16, its coupling to the optical system 16 includes a high precision holder 58. The fiber optics conductor holder 58 may be made of glass, ceramic or other material capable of being formed to a high degree of precision tolerance. The fiber optics light conductor 14 is prepared as shown in FIG. 9, with the distal part of its buffer sheath 61 removed. The holder 58 has a precision formed axial bore made up of two sections including an enlarged diameter proximal segment 60 and a narrow diameter distal segment 63. The bore 60, 63 receives the clad fiber of the light conductor 14. To prepare the optical fiber for attachment to the holder 58, the plastic buffer sheath 61 which typically surrounds and protects the optical fiber is removed to an extent such that the projecting portion 65 (see FIG. 9) of the fiber conductor can be extended through the distal small diameter bore 63 in the holder. Care is taken when stripping the buffer sheath 60 so as not to damage the layer of reflective cladding 67 about the core of the conductive fiber 14. The stripped end of the fiber assembly thus is inserted into the holder so that the stripped protruding portion 65 of the fiber extends into the small diameter bore 63 while the proximal portion containing the buffer sheath 61 is contained within the larger diameter portion 60 of the axial bore in the holder 58. The end of the optical fiber which protrudes beyond surface 62 of holder 58 may be finished flush with surface 62 of the holder 58. The foregoing arrangement serves to hold the aperture end 36 of the fiber flush with the distal end surface 62 of holder 58, against which the first tubular spacer 52 abuts. This arrangement establishes precisely the spacing between the aperture end 36 of the light conductor 14 and the spherical lens 28. The rigidity and precision with which the holder 58 can be made also assures precise alignment and positioning of the fiber along the optical axis of the system. The fiber optics light conductor 14 may be held in the holder 58 with an epoxy cement.

The spacers may be made of a thin-wall tubing (e.g: thin-wall tubing having outer diameter 0.040 inch and wall thickness 0.005 inch) which will not cause vignetting. For optimum radiopacity performance a radiopaque material such as tantalum is preferred as a spacer material.

The catheter body 10 is fitted over the narrower back end 64 of the holder 58 spaced a short distance from the shoulder 68 between the two parts of the holder. The glass tube 51 is bent over the shoulder 68, as by fusing the end 65 of the glass around the shoulder. A filler 66, which may be made of a plastic, such as Teflon (trademark for polytetrafluoroethylene), fills the annular space between the catheter body 10 and confronting end 65 of the glass tube 51. The outer diameter of the entire assembly, from the catheter body 10 to the glass tube 51, is substantially the same, providing a smooth uniform surface the entire length of the catheter, as is indicated in FIG. 1.

The concave surface 44 of the exit lens component 42 is formed after the assembly of the holder 64, lens components 38, 40, 42 and spacers 52, 54, 56 into the glass tube 51 has been completed. Pyrex brand glass No. 7740 is chosen as the material for the exit lens 42 and the glass tube 51. The exit lens 42 begins as a glass rod 1.5 mm long and 1.0 mm outer diameter with the end which will form the interior after assembly polished flat. When assembled into the glass tube 51, the exit lens 42 is fused to the glass tube, Pyrex brand glass being preferred because it has a lower softening temperature than other suitable optical glass materials. Such other materials can be used for the inner lens components 28 and 30. After fusing, the concave exit lens surface 44 is formed, and the exit end edge 55 of the glass tube is rounded to mate smoothly with the periphery of the concave surface.

Figure 13:
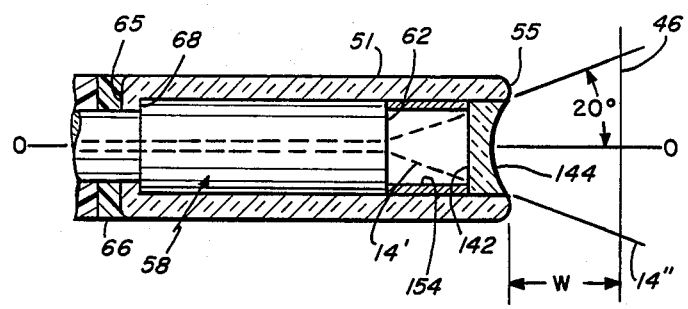
FIG. 13 is an axial-sectional view of another embodiment of an optical system.

In FIG. 13, the optical system illustrated comprises a single net-negative lens element 142 at the exit end 55 of the glass tube 51, separated precisely from the nearer transverse surface 62 of the light conductor holder 58 by a radiopaque spacer 154. Preferably the lens expands the light beam 14' exiting from the light conductor 14 to a beam 14" exiting from the lens at an angle of about 20° to the optical axis 0—0. The beam power parameters are adjusted so that in the working region W between the concave exit surface 144 and the nearby transverse plane 46 the radiant energy has the required density, substantially uniformly distributed to perform tissue removal according to the invention.

The aperture of the lens opening (44, 144) in the present invention is very close to the full outer diameter of the supporting envelope, namely, the tube 51, so as to provide an expanding beam that is just under the housing diameter close-in to the housing 51, for enabling the housing to be advanced into the hole that is being formed, as well as to maximize the energy that can be delivered through the miniature optical system 16.

From the foregoing it will be appreciated that the invention provides a catheter adapted to transmit and deliver radiant energy of a character adapted to etch or erode biological material, such as a vascular obstruction. The invention may be used with radiant energy in the visible, infra-red, ultra-violet and far-ultraviolet (200 nm) ranges. The invention embodies an arrangement for delivering the radiant energy in a manner which avoids the risk of perforating the wall of the vessel. It should be understood, however, that the foregoing description of the invention is intended merely to be illustrative thereof and that other modifications and embodiments will be apparent to those skilled in the art without departing from its spirit.

Having thus described the invention what we desire to claim and secure by letters patent is:

1. A method for recanalizing an obstructed lumen by removing successive layers of biological obstructing material so as to form a hole through said material by application of radiant energy comprising:
    providing a catheter having waveguide means, the catheter having a distally located emission aperture for emission of said radiant energy in a beam propagating along a beam axis, said emission aperture having cross-sectional dimensions corresponding substantially to cross-sectional dimension of the catheter;
    inserting said catheter into said lumen to locate the emission aperture in proximity to the obstruction;
    directing said radiant energy through the waveguide means to cause emission of said beam from said emission aperture;
    controlling said emitted beam to define an unfocused working region extending distally from said emission aperture and around said axis in which the density of said energy is sufficient to cause said removal and so that portion of the beam which propagates distally beyond the working region will have insufficient energy density to cause said removal;
    said working region defining a cross-section substantially large enough to enable the catheter to be passed through a hole formed by the working region, the working region having an axially depth not substantially greater than about cross-sectional dimension of the catheter;
    applying the working region of the beam to the obstructing material thereby to form a hole by removal of said material to a depth no greater than about the axial extent of said working region; and
    advancing said catheter through said hole.

2. A method as defined in claim 1 further comprising:
    providing said beam so that it has a pattern wherein the radiation diverges from said axis as it propagates along said axis beyond said working region.

3. A method as defined in claim 2 further comprising:
    providing said beam so that it has substantially uniform energy distribution around said axis.

4. A method as defined in each of claims 1 to 3 wherein said radiant energy comprises laser energy.

5. A method according to claim 1 wherein the properties of said energy are selected with respect to energy absorption properties of said obstructing material to provide that substantially all the energy in said working portion is consumed in causing said removal.

6. A method according to claim 5 wherein the frequency range of said energy is selected with respect to the predominant molecular constitution of said obstructing material so as to form said hole by ablative photo-decomposition of said obstructing material.

7. A method according to claim 1 in which said energy forms said hole by thermal vaporization of said obstructing material.

8. A method according to claim 1 in which the radiation is supplied to said obstructing material via an optical conductor.

9. A method according to claim 8 in which said radiation is supplied via a net-negative optical system.

10. A method according to claim 2 in which said radiant energy is applied to said working region through a net-negative optical system.

11. A method according to claim 1 in which said working region extends up to approximately 1.5 mm. along said axis.

12. A method according to claim 1 wherein said step of providing said beam of radiant energy comprises causing said beam to be emitted from an emission aperture in which said working region has a diameter at least as great as that of said emission aperture.

13. A method according to claim 2 in which said beam diverges to about 20° from said axis when said beam is propagated in a saline solution.

14. A method according to claim 8 for application to forming a hole through plaque in a vascular obstruction wherein said optical conductor is guided to said obstruction in a catheter having said optical system fixed at the distal end thereof.

15. A method according to claim 1 including the step of pulsing said radiant energy and adjusting the pulse parameters for forming said hole.

16. A method as defined in claim 8 further comprising:
    flouoroscopically locating and positioning the optical conductor with respect to the biological material.

17. A method of removing a biological obstruction by radiant energy comprising:
    providing a catheter having waveguide means for guiding said radiant energy from a source thereof, said catheter having a distally located emission aperture for emission of said radiant energy in a beam propagating along beam axis;
    forming said beam into a geometrically expanding pattern in which the energy distribution around said beam axis is substantially uniform whereby the energy density of said beam along said beam axis when applied to said obstruction decreases both exponentially and geometrically in a distally extending direction;
    the energy density in a working region of the beam within a first isothermal zone being sufficient to effect removal of the material forming the obstruction when said material is located in said region, the portion of the beam extending distally of said working region having insufficient energy density to effect said removal;
    said working region defining cross sectional dimensions large enough to enable the catheter to be passed therethrough, the working region having an axially extending depth not substantially greater than about the cross-sectional dimension of the catheter;
    whereby when said beam of energy is applied to the biological material said radiant energy will be effective to remove said material to a depth no greater than about the axial depth of said working region, thereby limiting said removal to a layer approximating the axial depth of said working region, and minimizing perforation of tissue located distal or radial to the isothermal boundary of said working region.

18. A method as defined in claim 17 wherein the properties of said energy are selected with respect to properties of said obstruction to provide that substantially all the energy in said working portion is consumed in causing said removal.

19. A method as defined in claim 18 wherein said step of forming said radiant energy into said beam pattern comprises:
    providing net-negative optical sensing means at the distal end of the waveguide means to shape the beam.

20. A method as defined in claim 19 wherein said step of providing lens means for shaping the beam comprises:
    passing the beam from the exit surface of an optical fiber conductor through an exit lens having a concave output surface.

21. A catheter for recanalizing an obstructed lumen by selectively removing sequential layers of biological obstructing material by radiant energy comprising:
    an elongate catheter body containing a flexible optical conductor;
    the proximal end of the catheter having means to enable said radiant energy to enter the flexible optical conductor;
    the distal end of the catheter having an emission aperture from which a beam of said radiant energy may be emitted, said emission aperture having a cross-sectional dimension which substantially corresponds to that of the distal end of the catheter;
    said catheter and emission aperture being constructed and arranged to shape the radiant energy beam emitted from the emission aperture to define an unfocused beam having a working region in which the density of energy is sufficient to cause said removal, and so that the portion of the beam extending distal to the working region has insufficient energy density to cause said removal; and
    the cross-sectional dimensions of the beam in the working region being no smaller than about the diameter of the distal end of the catheter thereby to enable the catheter to be passed through a recanalized hole formed by said working region, the axial depth of the working region being not substantially greater than the cross-sectional dimension of the distal end of the catheter.

22. A catheter as defined in claim 21 wherein said means for shaping the beam further comprises net-negative optical means at the distal end of the catheter.

23. A catheter as defined in claim 21 or 22 wherein said optical means encloses and isolates the exit end of the optical conductor to preclude contact of the exit end of the optical conductor with the biological material.

24. A catheter as defined in claim 21 or 22 wherein said optical means is constructed and arranged so that the beam emitted from the emission aperture will have substantially uniform energy distribution in a plane transverse to the direction of propagation of said energy.

25. A catheter as defined in claim 24 further comprising:

means for holding said exit end of the optical conductor and said optical means in a prescribed spatial relationship.

26. An optical system as defined in claim 25 in which the optical means includes an exit lens and in which a concave surface of said exit lens confronts said transverse plane.

27. A catheter as defined in claim 22 in further combination with a laser source of said radiant energy.

28. An optical system as defined in claim 25 further comprising:
   the optical means including an exit lens means having net negative optical power; and
   a spherical object lens between said exit end of said optical conductor and the exit lens means.

29. An optical system as defined in claim 28 in which said exit lens is bi-concave.

30. An optical system as defined in claim 28 in which said exit lens is plano-concave.

31. An optical system as defined in claim 25 including a tubular housing for holding said end and said lens means in said spatial relationship.

32. An optical system as defined in claim 31 including a radiopaque tubular spacer within said housing.

33. An optical system as defined in claim 31 in which the aperture of said exit lens means is substantially equal to the outer diameter of said tubular housing.

34. An optical system as defined in claim 28 including a plano-concave lens between said object lens and said exit lens, a first tubular spacer within said housing between said object lens and said plano-concave lens, and a second tubular spacer within said housing between said plano-concave lens and said exit lens.

35. An optical system as defined in claim 31 in which said exit lens means and said housing are made of glass capable of being fused together.

36. An optical system as defined in claim 35 in which said glass is a predominantly borosilicate glass.

37. An optical system as defined in claim 25 in which said holding means includes a part which is radiopaque.

38. An optical system as defined in claim 26 in which said holding means includes a rigid holder for said exit end of said optical conductor and spacer means for fixing the distance between said holder and said exit lens means.

39. An optical system as defined in claim 38 including a tubular housing enclosing said exit lens means, said spacer means and a part of said receiver.

40. An optical system as defined in claim 31 in which said housing is radio-transparent and includes a part which is radiopaque.

41. An optical system as defined in claim 40 in which said part is a tubular spacer for an optical component of said system.

42. An optical system as defined in claim 25 including a tubular housing made of a glass that is fusible to said exit lens means, in which the edge of said housing at the periphery of said lens means is rounded to form a smooth boundary with said lens means.

43. A catheter as defined in claim 21 wherein the catheter body has a lumen extending there through from its proximal to its distal portions, the catheter body having aperture means at its distal portion in communication with the lumen and means at the proximal end of the catheter for making a fluid connection to the lumen.

44. A catheter as defined in claim 43 wherein the optical conductor extends through the lumen.

45. A catheter as defined in claim 23 further comprising means for holding the exit end of the optical conductor and lens means in prescribed spatial relation, said holding means comprising:
   a rigid tubular holder having a proximal end and distal end, the holder having a bore extending therethrough to receive the distal end of the optical conductor, said optical conductor being secured rigidly within the bore of the holder;
   the exit end of the optical conductor being flush with the distal end of the holder;
   a tubular housing for receiving at least a portion of the holder and the proximal end of the housing and for receiving the lens means at the more distal regions of the housing;
   spacer means within the tubular housing and in engagement with the lens means and the distal end of the holder to space precisely the holder and conductor carried thereby with respect to the lens means; and
   means for securing holder to the tubular housing.

46. A catheter as defined in claim 45 further comprising:
   the holder having a shouldered portion between its ends;
   said tubular holder being formed to engage the shoulder to secure the holding means to the tubular holder.

47. A catheter as defined in claim 46 further comprising:
   the proximal end of the holding means being received in the lumen at the distal end of the catheter body, the juncture region between the distal end of the catheter body and the proximal end of the tubular housing being filled to present a smooth and continuous outer surface along said catheter.

48. A catheter as defined in claim 21 wherein the length of the working region along the axis is no greater than approximately 1.5 millimeters.

49. A method of removing a biological obstruction by radiant energy comprising:
   providing a catheter having waveguide means for guiding said radiant energy from a source thereof, said catheter having a distally located emission aperture for emission of said radiant energy in a pattern propagating along an axis;
   forming said emitted radiant energy into a geometrically expanding pattern in which the energy distribution around said axis is substantially uniform whereby the energy density of said emitted energy along said axis when applied to said obstruction decreases both exponentially and geometrically in a distally extending direction;
   the energy density in a working region of the emitted energy within a first isothermal zone being sufficient to effect removal of the material forming the obstruction when said material is located in said region, the portion of the emitted energy extending distally of said working region having insufficient energy density to effect said removal;
   said working region defining cross-section dimensions large enough to enable the catheter to be passed therethrough, the working region having an axially extending depth not substantially greater than about the cross-sectional dimension of the catheter;
   whereby when said emitted energy is applied to the biological material said radiant energy will be effective to remove said material to a depth no greater than about the axial depth of said working region, thereby limiting said removal to a layer approximating the axial depth of said working region, and minimizing perforation of tissue located distal or radial to the isothermal boundary of said working region.

50. A catheter for recanalizing an obstructed lumen by selectively removing sequential layers of biological obstructing material by radiant energy comprising:

an elongate catheter body containing a flexible optical conductor;

the proximal end of the catheter having means to enable said radiant energy to enter the flexible optical conductor;

the distal end of the catheter having an emission aperture from which said radiant energy may be emitted, said emission aperture having a cross-sectional dimension which substantially corresponds to that of the distal end of the catheter;

said catheter and emission aperture being constructed and arranged to shape the radiant energy emitted from the emission aperture to define an unfocused pattern having a working region in which the density of energy is sufficient to cause said removal, and so that the portion of the emitted energy extending distal to the working region has insufficient energy density to cause said removal; and the cross-sectional dimensions of the emitted energy in the working region being no smaller than about the diameter of the distal end of the catheter thereby to enable the catheter to be passed through a recanalized hole formed by said working region, the axial depth of the working region being not substantially greater than the cross-sectional dimension of the distal end of the catheter.

* * * * *